(12) United States Patent
Overes et al.

(10) Patent No.: US 10,383,742 B2
(45) Date of Patent: Aug. 20, 2019

(54) INTERVERTEBRAL IMPLANT

(71) Applicant: 41medical AG, Bettlach (CH)

(72) Inventors: Tom Overes, Langendorf (CH); Robert Frigg, Bettlach (CH)

(73) Assignee: 41medical AG, Bettlach (CH)

( * ) Notice: Subject to any disclaimer, the term of this patent is extended or adjusted under 35 U.S.C. 154(b) by 56 days.

(21) Appl. No.: 15/504,207

(22) PCT Filed: May 6, 2015

(86) PCT No.: PCT/CH2015/000075
§ 371 (c)(1),
(2) Date: Feb. 15, 2017

(87) PCT Pub. No.: WO2016/026057
PCT Pub. Date: Feb. 25, 2016

(65) Prior Publication Data
US 2017/0231778 A1    Aug. 17, 2017

(30) Foreign Application Priority Data

Aug. 18, 2014  (WO) ............... PCT/CH2014/000122
Mar. 18, 2015  (CH) ........................................ 379/15
Mar. 23, 2015  (WO) ............... PCT/CH2015/000047

(51) Int. Cl.
*A61F 2/44* (2006.01)
*A61F 2/46* (2006.01)
*A61F 2/30* (2006.01)

(52) U.S. Cl.
CPC ............ *A61F 2/4425* (2013.01); *A61F 2/447* (2013.01); *A61F 2/4455* (2013.01);
(Continued)

(58) Field of Classification Search
CPC .................................................. A61F 2/44–447
(Continued)

(56) References Cited

U.S. PATENT DOCUMENTS

| 6,610,089 B1 * | 8/2003 | Liu ...................... A61B 17/025 |
| | | 623/17.11 |
| 8,628,577 B1 * | 1/2014 | Jimenez ............... H05K 999/99 |
| | | 623/17.15 |

(Continued)

*Primary Examiner* — Nicholas J Plionis
(74) *Attorney, Agent, or Firm* — Rankin, Hill & Clark LLP

(57) ABSTRACT

Intervertebral implant (1) comprising (i) a first elongated implant member (20) with a longitudinal axis (221), an upper surface (222) and a lower surface (223) for apposition to the endplates of two adjacent vertebrae, and with a lateral circumferential surface (224) and (ii) a second elongated implant member (30) with a longitudinal axis (321), an upper surface (322) and a lower surface (323) for apposition to the same endplates and with a lateral circumferential surface (324). Said elongated implant members (20, 30) are rotatably coupled to a central body (10) for rotation in a central plane (101 essentially parallel to said upper and lower surfaces. Further, a) said first and second elongated implant members ($_2$0, 30) comprise each an inner end portion (225;325) which comprises a segment of a toothed wheel (220;320) with gear teeth (23;33) and with an axis of rotation (227;327) essentially orthogonal to the central plane of the intervertebral implant; and a free outer portion (226; 326); and whereby said free outer portions (226;3$_{26}$) of said first and second elongated implant members (20, 30) are rotatable around the axis of rotation (227;327) of the segment of a toothed wheel (220;320) of their respective inner end portions (225;325).

17 Claims, 12 Drawing Sheets

(52) U.S. Cl.
CPC .......... *A61F 2/4465* (2013.01); *A61F 2/4611* (2013.01); *A61F 2/442* (2013.01); *A61F 2002/3054* (2013.01); *A61F 2002/3055* (2013.01); *A61F 2002/30179* (2013.01); *A61F 2002/30378* (2013.01); *A61F 2002/30471* (2013.01); *A61F 2002/30507* (2013.01); *A61F 2002/30523* (2013.01); *A61F 2002/30525* (2013.01); *A61F 2002/30545* (2013.01); *A61F 2002/30579* (2013.01); *A61F 2002/30593* (2013.01); *A61F 2002/30616* (2013.01); *A61F 2002/4629* (2013.01); *A61F 2310/00023* (2013.01)

(58) Field of Classification Search
USPC ............................................. 623/17.11–17.16

See application file for complete search history.

(56) References Cited

U.S. PATENT DOCUMENTS

| | | | |
|---|---|---|---|
| 9,675,466 B2* | 6/2017 | Overes | A61F 2/442 |
| 2004/0088054 A1 | 5/2004 | Berry | |
| 2005/0021144 A1* | 1/2005 | Malberg | A61F 2/442 623/17.11 |
| 2006/0235423 A1* | 10/2006 | Cantu | A61B 17/8858 606/90 |
| 2007/0225808 A1 | 9/2007 | Warnick | |
| 2011/0054616 A1* | 3/2011 | Kamran | A61F 2/4465 623/17.12 |
| 2012/0197299 A1 | 8/2012 | Fabian, Jr. | |
| 2012/0209386 A1* | 8/2012 | Triplett | A61F 2/4465 623/17.16 |
| 2012/0310350 A1* | 12/2012 | Farris | A61F 2/4455 623/17.16 |
| 2013/0079883 A1 | 3/2013 | Butler et al. | |

\* cited by examiner

INTERVERTEBRAL IMPLANT

BACKGROUND OF THE INVENTION

1. Field of the Invention

The invention relates to an intervertebral implant according to the preamble of claim 1, to a kit according to the preamble of claim 41 and to a method for replacing or repairing intervertebral disks according to the preamble of claim 44.

Low back pain is a common disease for example caused by herniated discs, compressed nerve roots, degenerative discs or joint disease. If a patient has this severe pain and does not respond to conservative treatment, spinal fusion is an option to eliminate the pain. Spinal fusion is a surgical technique, wherein two or more vertebrae are joined together. Spinal fusion interventions are also performed to correct back deformities.

With inter-body fusion often an intervertebral spacer or device is placed between the involved vertebrae after removal of the intervertebral disc. The intervertebral device corrects the spine alignment and restores the disc height.

Common intervertebral devices are made from titanium alloys or polyetheretherketone (PEEK). Often these devices comprise pockets that can be filled with bone graft material or artificial graft substitute. The fusion itself takes place when the bone of the endplates grows into and through the intervertebral device. Finally both vertebrae are grown together. Often, additionally, a pedicle system provides additional posterior stabilisation. Intervertebral fusion devices can be implanted with various approaches, for example from the anterior, the posterior or the lateral side.

Over the past years minimal invasive techniques have been introduced. The advantages of the minimal invasive techniques are less soft tissue trauma resulting in a faster recovery. Other complications are reduced as well. In minimal invasive techniques the implant is brought into position between the vertebrae through a small incision with small instruments. Still the intervertebral device must have a sufficient large foot-print to translate the forces between the vertebrae before complete fusion has taken place. If a device is too small, it will sink into or break through the endplate of the vertebra, and the initially restored height is lost.

2. Description of the Related Art

US 2012/0197299 A1 (Henry Fabian JR) describes an implant comprising two members being pivotal relative to each other in a scissor-like manner and each comprising two limbs. The implant may be inserted into a vertebral space in a first non-expanded configuration, where all limbs are adjacent to each other, and which may then subsequently be deployed to a second expanded configuration having a larger foot-print.

US 2013/0079883 (Micheal Butler et al.) describes a radially expandable intervertebral implant including a plurality of filigree members that are interconnected and a deployment mechanism arranged on one end of the link chain.

These known implants have the disadvantage that they comprise either a number of articulations arranged between the interlinked members or a relatively complicated articulation mechanism is necessary to couple the two scissor-like deployment members both resulting in a reduction of the rigidity and compactness of the implant.

BRIEF SUMMARY OF THE INVENTION

It is the object of the invention to provide an intervertebral implant having an improved rigidity of the deployable members as well as a compact and stable deployment mechanism.

The invention solves the posed problem with an intervertebral implant comprising the features of claim 1, with a kit comprising the features of claim 41 and with a method for replacing or repairing intervertebral disks comprising the features of claim 44.

Further advantageous embodiments of the invention can be commented as follows:

In a special embodiment said central body is in the form of a segmental arc and said elongated implant members are coupled to said central body at an apex of said segmental arc.

In a further embodiment the elongated implant members are in the shape of a segmental arc and substantially abut with said central body along their entire length in an unexpanded configuration of the intervertebral implant.

In a further embodiment said elongated implant members and the central body form a substantially X-shaped footprint in an expanded configuration of the intervertebral implant.

In another embodiment the elongated implant members and the central body are substantially straight and form a substantially K-shaped footprint in an expanded configuration of the intervertebral implant.

In again another embodiment the intervertebral implant comprises a third elongated implant member with a longitudinal axis, an upper surface and a lower surface for apposition to the same endplates and with a lateral circumferential surface, and rotatably coupled to the central body. The third elongated implant member essentially comprises an inner end portion which comprises a segment of a toothed wheel with gear teeth and with an axis of rotation essentially orthogonal to the central plane of the intervertebral implant and a free outer portion. Thereby the free outer portion of the third second elongated implant member is rotatable around the axis of rotation of the segment of a toothed wheel of its respective inner end portion and the segment of a toothed wheel of said third elongated implant member is in engagement with a segment of a toothed wheel of one of the first and second elongated implant members. Furthermore, the segment of a toothed wheel of said third elongated implant member is located in the center portion of said intervertebral implant from which the elongated implant members are deployable.

In yet a further embodiment the intervertebral implant comprises more than three elongated implant members wherein said implant members are rotatably coupled to the central body, and wherein the segment of a toothed wheel of at least one of said elongated implant members is in engagement with the segment of a toothed wheel of two others of said elongated implant members.

In another embodiment the intervertebral implant comprises three elongated implant members, wherein said three elongated implant members form a substantially Y-shaped footprint in an expanded configuration.

In a further embodiment the intervertebral implant comprises four elongated implant members, wherein said four elongated implant members form a substantially X-shaped footprint in an expanded configuration of the intervertebral implant.

Preferably, the central body is provided with driving means for rotating said first and second elongated implant members around their respective axis of rotation from a collapsed configuration, suitable for insertion into an intervertebral space between two adjacent vertebrae, to an expanded configuration when positioned between the endplates of two adjacent vertebrae.

In a further embodiment the driving means are arranged parallel to the central plane.

In a further embodiment the driving means comprise a dowel having a ball head at one end, said ball head cooperating with a first channel located on the inside of said first elongated implant member, such as to impart motion onto said first elongated implant member for rotating said first elongated implant member relative to said central body around its axis of rotation.

In again a further embodiment the driving means comprises a dowel having a first structure on one end, said first structure cooperating with a second structure on at least one of said elongated implant elements in a form-fitting manner, such as to rotate said one elongated implant member relative to said central body.

In another embodiment the driving means comprise a worm arranged in said central body, said worm engaging a segment of a toothed wheel arranged on one of said elongated implant members.

In another embodiment each segment of a toothed wheel arranged on said elongated implant members is configured as a circular segment of a toothed wheel.

In a further embodiment at least one segment of a toothed wheel arranged on said elongated implant members is configured as a non-circular segment of a toothed wheel. The segments of a toothed wheel can exemplarily be configured as segments of oval toothed gears, segments of a logarithmic spiral toothed gears, segments of elliptically shaped toothed gears or even as segments of specially shaped toothed gears that roll and mesh properly with other toothed gears of any shape.

In a further embodiment the expansion of the intervertebral implant is reversible.

In a further embodiment the expansion is of a continuous nature.

In again a further embodiment said elongated implant members are of equal length.

In another embodiment the expansion is symmetric.

In another embodiment said elongated implant members are of unequal length.

In again another embodiment said elongated implant members comprise at least one open cavity or pocket for receiving bone graft material.

In a further embodiment said elongated implant members are configured as cages for receiving bone graft material.

In a further embodiment the upper surfaces and lower surfaces of the elongated implant members are flush with each other.

In another embodiment the upper surfaces and the lower surfaces of said elongated implant members are arranged at an angle different from 0° to each other. Preferably, the angle is larger than 1°, preferably larger than of 2°.

In a further embodiment the angle is smaller than 15°, preferably smaller than 10°.

In another embodiment the lower surfaces and the upper surfaces of said elongated implant members are parallel to each other.

In another embodiment the elongated implant members are substantially parallel in an unexpanded configuration of the intervertebral implant.

In a further embodiment the edges between the lateral circumferential surface and the upper surface, respectively the lower surface of said elongated implant members are at least partially rounded and/or chamfered. This avoids damaging the endplates of the two adjacent vertebrae during expansion or contraction of the intervertebral implant.

In a further embodiment the intervertebral implant is configured in a compact manner with a center portion from which the elongated implant members are deployed.

In again a further embodiment a cross-section through the intervertebral implant along the central plane has a total area excluding any open cavities or pockets of at least 600 mm$^2$, preferably of at least 800 mm$^2$ in the case of an intervertebral implant including three or four elongated implant members.

In another embodiment a cross-section through the intervertebral implant along the central plane has a total area excluding any open cavities or pockets of at least 250 mm$^2$, preferably of at least 350 mm$^2$ in the case of an intervertebral implant including two elongated implant members.

In another embodiment the elongated implant members are made from a plastic material, preferably PEEK and the driving means are made from a metal, preferably from titanium or a titanium alloy.

In again another embodiment the expansion of the elongated implant members is limited by a stop member.

In a further embodiment the range of rotation of the elongated implant members is limited to maximum 80°, preferably to maximum 50°. Typical values for a lateral cage (LLIF/XLIF) are 40°-45° and for a transforaminal cage (TLIF) 25°-35°. In a further embodiment the ratio of the perimeter length of the deployed implant to the perimeter length of the undeployed implant is at least 1.25, preferably at least 1.4 in the case of an intervertebral implant comprising four elongated implant members.

Typical values for the perimeter length are:

Four elongated implant members closed=130 mm/four elongated implant members open=200 mm: 200/130=1.5. The theoretical outer perimeter of the four elongated members open implant is 1.5 times the theoretical perimeter of the closed implant.

In another embodiment the ratio of the perimeter length of the deployed implant to the perimeter length of the undeployed implant is at least 1.15, preferably at least 1.3 in the case of an intervertebral implant comprising two elongated implant members.

Typical values for the perimeter length are:

Two elongated implant members closed: 120 mm, open 150 mm. 150/120=1.25. The theoretical outer perimeter of the two elongated member open implant is 1.15 times the theoretical perimeter of the closed implant.

In another embodiment in the central body forms a central base portion of the intervertebral implant.

In a further embodiment the intervertebral implant comprises means for deploying the elongated implant members. Exemplarily but not limiting the means for deploying the elongated implant members can be rounded or chamfered edges at the free outer portions of one or two elongated implant members, preferably the edges extending from the upper surfaces to the lower surfaces so that an instrument (not shown) can be introduced between the two free outer portions and e.g. rotated so as to spread the elongated implant members.

According to the invention the intervertebral implant comprises a first elongated implant member and a second elongated implant member. Each of said elongated implant members is rotatably coupled to a central base portion and comprises a first end with an axis of rotation and circumferentially arranged gear teeth. The gear teeth of the first implant member are interlocked into the gear teeth of the second implant member.

By rotating one of said two elongated implant members around its axis of rotation, the other elongated implant member is also moved around its axis of rotation. The transmission of the rotation movement by means of a gear tooth system ensures a uniform transmission of the rotation movement and hence allows a uniform deployment of both elongated implant members.

The intervertebral implant according to the present invention is expandable in a plane which is essentially parallel to the surfaces of the vertebral bodies facing towards the intervertebral space the intervertebral implant is to be implanted into. Hence, expansion of the inventive intervertebral implant only results in an expansion of the overall foot-print of the intervertebral implant while the distance between the adjacent vertebrae is not increased.

The interlocking of the gear teeth of the first elongated implant member with the gear teeth of the second elongated implant member results in a kind of gear or transmission system, wherein upon rotation of one of the two elongated implant member in one direction, the other elongated implant member is rotatably moved into an opposite direction.

Preferably, both elongated implant members have gear teeth which are arranged at the same distance from the axis of rotation, i.e. the gear ratio between the elongated implant members is 1:1. Hence, rotation of one of said elongated implant member by a specific angle will provoke a rotation of the other elongated implant member by the same angle.

Alternatively, the distance between the teeth to the axis of rotation of at least one of the elongated implant members may be chosen to be unequal to the distance of the other elongated implant member. This results in different rotational speeds of the elongated implant members, i.e. to a gear ratio which is higher or lower than 1:1.

Provision of gear teeth allows the expansion of the intervertebral implant by exerting a pulling force on any of the two elongated implant members, as rotation of any of said elongated implant members will exert a rotational force onto the other elongated implant member.

The axes of rotation of both elongated implant members are preferably parallel to each other. The gear teeth are arranged around said axes along at least a portion of a circle. Preferably, the gear teeth are arranged around a half circle or a quadrant of a circle, said circle having its centre located on the axis of rotation of the respective elongated implant member.

The elongated implant members preferably have a base area which is in the form of a trapezoid, more preferably of a right angle trapezoid. Further preferably, at least one corner area of each of said elongated implant members is rounded such as to ease the insertion of the intervertebral implant without causing any irritation to the annulus. The circumferentially arranged gear teeth are preferably located on one of the smaller sides of the elongated implant members.

The elongated implant members each preferably have a lower surface and an upper surface configured to contact bone of two adjacent vertebral bodies. Said lower and said upper surface are spaced from each other by a thickness which preferably corresponds to the natural height of an intervertebral disc. Both surfaces may be arranged parallel to each other, however preferably, the thickness of the elongated implant members varies from one end of the intervertebral implant which is to be arranged on a ventral side of the intervertebral space to the side which is to be arranged on a dorsal side of the intervertebral space. This allows conforming the shape of the intervertebral implant to the natural shape of the intervertebral space. The arc/kidney shaped configuration of the intervertebral implant also permits to facilitate insertion of the intervertebral implant by using a transforaminal technique.

Said upper surface and said lower surface preferably include a structure which enhances the friction between the surfaces and the bone of the adjacent vertebral bodies. Said structure may e.g. comprise a multitude of ribs, burls, pyramid shape protrusions or the like. Such a structure enhances the friction between the elongated implant members and the vertebral bone, hence safely anchoring the intervertebral implant in the intervertebral space.

The central base portion constitutes the attachment point of both elongated implant members. Hence, each elongated implant member is rotatably coupled to said central base portion by means of its rotation axis.

Preferably, said elongated implant members each include a recess into which a part of the central base portion may be inserted. This allows configuring the intervertebral implant with flush surfaces. More preferably, said recess is arranged centrally between the upper surface and the lower surface of each of said elongated implant members. This allows to insert parts of the central base portion into said recesses and to rotatably couple the central base portion on both sides with each of said elongated implant members by means of a peg or pin, hence increasing the stability of the coupling between the central base plate and each of the elongated implant members. Preferably, circumferentially arranged gear teeth are arranged on both sides of said recess.

Preferably, the intervertebral implant is made of titanium or a titanium alloy. Further preferably, the intervertebral implant may be made of a biocompatible polymer, most preferably of polyetheretherketone (PEEK) or of fiber reinforced polyetheretherketone. Further, the intervertebral implant may be made of a combination of materials. Preferably, the base portion is a body in the form of a segmental arc and said elongated implant members are coupled to the base portion at an apex of said segmental arc. Provision of the base portion and the elongated implant members in the form of segmental arcs has the advantage that the intervertebral implant may be easily inserted between two adjacent implant bodies, as the arced shape substantially conforms to the curvature of the rim of the spinal bodies.

As understood herein, a segmental arc is a segment of a curve, especially of a circle. The segmental arc thereby spans less than 180°, i.e. less than a semicircle. Alternatively, the segmental arc may also be in the form of a segment of an ellipse, a so-called elliptical arc. By coupling the elongated implant elements to the apex, both elongated implant elements are symmetrically arranged on said central base portion.

In a preferred embodiment, the elongated implant members are in the shape of a segmental arc and substantially abut with said base portion along their entire length in an initial an unexpanded configuration. This allows providing an intervertebral implant having a very small footprint in the unexpanded configuration. Hence the size of the intervertebral implant for implantation is small, allowing the insertion of the intervertebral implant through an incision with minimal dimensions.

Preferably, said elongated implant members and said central base portion form a substantially X-shaped footprint in an expanded configuration. As the central base portion and the elongated implant members preferably are in the form of a segmental arc, the "legs" of the X-shape will be curved. The centre of the X-shape is thereby defined by the apex of the central base portion to which the elongated implant members are coupled. Provision of such a configuration allows having a large footprint of the intervertebral implant in the expanded configuration.

In an alternatively preferred embodiment, the elongated implant members and the central base portion are substantially straight and form a substantially K-shaped footprint in an expanded configuration. Preferably, the elongated implant members are coupled to the central base portion at a location which is in the middle of the length of said central base portion, such that the elongated implant members are symmetrically arranged onto said central base portion.

The intervertebral implant preferably comprises at least one pocket for receiving bone graft material. Preferably said at least one pocket is arranged in one of the elongated implant members and spans the entire thickness of said elongated implant member, i.e. the pocket is in the form of a bore or hole spanning the entire thickness of said elongated implant member. Provision of such a pocket allows applying bone graft material linking both vertebrae together. This enhances the ingrowth of bone through the intervertebral implant. Preferably, each of said elongated implant members comprises at least one pocket for receiving bone ingrowth material.

Preferably, said intervertebral implant comprises elongated implant members of unequal length. This allows tailoring the intervertebral implant to different intervertebral spaces, e.g. depending on the type of vertebrae adjacent said intervertebral space. For example, the configuration of the lengths of the elongated implant members may be different if the intervertebral implant is to be implanted between thoracic vertebrae or between lumbar vertebrae.

Preferably, the intervertebral implant comprises a dowel having a ball head on one end, said ball head cooperating with a first channel located on the inside of the first elongated implant member, such as to impart motion onto said first elongated implant member for rotating said first elongated implant member relative to said central base structure around its axis of rotation.

Preferably, said dowel is cylindrical and said ball head has a first diameter. The first channel is preferably cylindrical and has a diameter which corresponds to the first diameter of the ball head. Preferably, the ball head is form-fittingly engaged within said channel, such that pulling and pushing forces acting on said dowel are transmitted onto said first elongated implant member.

This provides a simple and easy to use drive for the intervertebral implant, as a linear movement of the dowel will exert a pulling or pushing force on said first elongated implant member, resulting in a rotational movement of said first elongated implant member.

Alternatively, the dowel may comprise a single protrusion which engages into a single groove provided on said one elongated implant member.

Further, any suitable type of form-fit interaction may be used for cooperation of said dowel with the elongated implant member.

Preferably, the dowel is arranged in a second channel provided in said central base portion, said second channel having an opening allowing the insertion of the instrument by a surgeon, such as to push or pull the dowel to move it relative to said central base portion.

Preferably, said dowel comprises a drive at a second end arranged opposite of said first end, such that an instrument to move said dowel may be inserted into said drive. More preferably, an outer thread is arranged on said second end, said outer thread cooperating with a matching inner thread provided in said central base portion of the intervertebral implant, preferably in said second channel. Hence, by imparting a turning motion to said dowel, the dowel will be linearly moved relative to said central base portion, thus imparting a pulling or pushing force onto said elongated implant member by means of the form-fit interaction of the two ball head within the first channel. Preferably, each of the two elongated implant members as well as the central base portion comprises a lower surface and an upper surface, said upper surfaces and said lower surfaces being flush with each other.

Hence, both elongated implant members as well as the central base portion may contact and thus support adjacent vertebral bodies, as they form a contiguous upper and lower plane. Preferably, the central base portion comprises at least one part with surfaces which are not flush with the lower and upper surfaces of the elongated implant members, but spaced apart from these. Preferably, said at least one part is located at the apex of the segmental arc of the central base portion. The two elongated implant members are preferably coupled to the at least one part, while the at least one part may be engaged into the recess of said elongated implant members.

Preferably, said upper and said lower surfaces are arranged at an angle to each other. Said angle more preferably is from 0° to 15°.

The two surfaces are located on the two sides of the elongated implant members intended to be in contact with the bone of adjacent vertebrae. By varying the angle of the upper and lower surfaces relative to each other allows to restore the natural lordotic or kyphotic curvature of the spine.

Preferably, the lower surfaces and the upper surfaces of said elongated implant members and of said central base portion are parallel to each other.

According to further embodiments of the invention the intervertebral implant comprises three or more elongated implant members. Each of said implant members is rotatably coupled to a central base portion and comprises a first end with an axis of rotation and circumferentially arranged gear teeth. The gear teeth of at least one of said implant members is interlocked into said gear teeth of the two other implant members.

The advantages of the intervertebral implant according to the invention can be commented as follows:

By rotating one single elongated implant member around its axis of rotation, the at least two other elongated implant members are also moved around their respective axes of rotation. The transmission of the rotation movement by means of a gear tooth system ensures a uniform transmission of the rotation movement and hence allows a uniform deployment of all the elongated implant members.

The intervertebral implant according to the present invention is expandable in a plane which is essentially parallel to the surfaces of the vertebral bodies facing towards the intervertebral space the intervertebral implant is to be implanted into. Hence, expansion of the inventive intervertebral implant only results in an expansion of the overall foot-print of the intervertebral implant while the distance between the adjacent vertebrae is not increased.

The interlocking of the gear teeth of the at least one elongated implant member with the gear teeth of the two other elongated implant members results in a kind of gear system, wherein upon rotation of the at least one elongated implant member in one direction, the two other elongated implant members are rotatably moved into an opposite direction.

Preferably, all the elongated implant members have gear teeth which are arranged at the same distance from the axis of rotation, i.e. the gear ratio between any of the elongated implant members is 1:1. Hence, rotation of said at least one elongated implant member by a specific angle will provoke a rotation of the other elongated implant members by the same angle.

Alternatively, the distance between the teeth to the axis of rotation of at least one of the elongated implant members may be chosen to be unequal to the distance of the other elongated implant members. This results in different rotational speeds of the elongated implant members, i.e. to a gear ratio which is higher or lower than 1:1.

Provision of gear teeth for each elongated implant member interlocking with each other allows the expansion of the intervertebral implant by exerting a pulling force on any of the elongated implant members, as rotation of any of said elongated implant members will exert a rotational force onto all the other elongated implant members.

The axes of rotation of each of the elongated implant members are preferably parallel to each other. The gear teeth are arranged around said axes along at least a portion of a circle. Preferably, the gear teeth are arranged around a half circle or a quadrant of a circle, said circle having its centre located on the axis of rotation of the respective elongated implant member.

The elongated implant members preferably have a base area which is in the form of a trapezoid, more preferably of a right angle trapezoid. Further preferably, at least one corner area of each of said elongated implant members is rounded such as to ease the insertion of the intervertebral implant without causing any irritation to the annulus. The circumferentially arranged gear teeth are preferably located on one of the smaller sides of the elongated implant members.

The elongated implant members each preferably have a lower surface and an upper surface configured to contact bone of two adjacent vertebral bodies. Said lower and said upper surface are spaced from each other by a thickness which preferably corresponds to the natural height of an intervertebral disc. Both surfaces may be arranged parallel to each other, however preferably, the thickness of the elongated implant members varies from one end of the intervertebral implant which is to be arranged on a ventral side of the intervertebral space to the side which is to be arranged on a dorsal side of the intervertebral space. This allows conforming the shape of the intervertebral implant to the natural shape of the intervertebral space.

Said upper surface and said lower surface preferably include a structure which enhances the friction between the surfaces and the bone of the adjacent vertebral bodies. Said structure may e.g. comprise a multitude of ribs, burls, pyramid shape protrusions or the like. Such a structure enhances the friction between the elongated implant members and the vertebral bone, hence safely anchoring the intervertebral implant in the intervertebral space.

The central base portion constitutes the attachment point of all elongated implant members. Hence, each elongated implant member is rotatably coupled to said central base portion by means of its rotation axis. The central base portion is preferably in the form of a plate. Preferably, said central base portion has a polygonal base area with a number of corners which corresponds to the number of elongated implant members. E.g. if the intervertebral implant comprises three elongated implant members, the central base portion will be in the form of a triangle, whereas if the intervertebral implant comprises five elongated implant members, the central base portion will be in the form of a pentagon.

Preferably, said three or more elongated implant members each include a recess into which a corner of the central base portion may be inserted. This allows configuring the intervertebral implant with flush surfaces. More preferably, said recess is arranged centrally between the upper surface and the lower surface of each of said elongated implant members. This allows to insert the corners of the central base portion into said recesses and to rotatably couple the central base portion on both sides with each of said elongated implant members by means of a peg or pin, hence increasing the stability of the coupling between the central base plate and each of the elongated implant members. Preferably, circumferentially arranged gear teeth are arranged on both sides of said recess.

Preferably, the intervertebral implant is made of titanium or a titanium alloy. Further preferably, the intervertebral implant may be made of a biocompatible polymer, most preferably of polyetheretherketone (PEEK) or of fiber reinforced polyetheretherketone. Further, the intervertebral implant may be made of a combination of materials.

Further advantageous embodiments of the invention can be commented as follows:

Preferably, the elongated implant members are substantially parallel in an initial and unexpanded configuration. This allows minimizing the size of the intervertebral implant for implantation, hence allowing the insertion of the intervertebral implant through an incision with small dimensions.

Preferably, the intervertebral implant comprises four elongated implant members, wherein said four elongated implant members from a substantially X-shaped footprint in an expanded configuration. Provision of the intervertebral implant in the shape of an X provides a large foot-print of the intervertebral implant once expanded, hence allowing a good distribution of the loads transmitted between the adjacent vertebrae via said intervertebral implant.

In alternative, preferred embodiment, the intervertebral implant comprises three elongated implant members, wherein said three elongated implant members from a substantially Y-shaped footprint in an expanded configuration. This shape may be more suited in certain specific applications. Further, a Y-shaped implant allows an even distribution of the loads transmitted between the adjacent vertebrae via said intervertebral implant. A person having skill in the art will recognize that only one elongated implant member will cooperate with the two other elongated implant members, as otherwise no expansion would be possible.

The intervertebral implant preferably comprises at least one pocket for receiving bone graft material. Preferably said at least one pocket is arranged in one of the elongated implant members and spans the entire thickness of said elongated implant member, i.e. the pocket is in the form of a bore or hole spanning the entire thickness of said elongated implant member. Provision of such a pocket allows applying bone graft material linking both vertebrae together. This enhances the ingrowth of bone through the intervertebral implant. Preferably, each of said elongated implant members comprises at least one pocket for receiving bone ingrowth material.

Preferably, said intervertebral implant comprises elongated implant members of unequal length. This allows tailoring the intervertebral implant to different intervertebral spaces, e.g. depending on the type of vertebrae adjacent said intervertebral space. For example, the configuration of the lengths of the elongated implant members may be different if the intervertebral implant is to be implanted between thoracic vertebrae or between lumbar vertebrae.

The intervertebral implant preferably comprises a worm arranged in said central base portion, said worm engaging a second set of gear teeth arranged on one of said elongated implant members.

Hence, a worm-gear type drive of the intervertebral implant may be realized. The worm preferably includes a drive to be connected with an appropriate instrument, thus enabling the expansion of the intervertebral implant by a surgeon by the use of the instrument.

Preferably, the worm is of the self-locking type. This secures the elongated implant members from any movement towards the initial and unexpanded configuration due to forces exerted on any of said elongated implant members. However, further expansion or collapse of the intervertebral implant by means of the instrument remains possible. Preferably, the worm is arranged in a channel provided in said central base portion, said channel having an opening allowing the insertion of the instrument by a surgeon.

In an alternatively preferred embodiment, the intervertebral implant comprises a dowel having a first structure on one end, said first structure cooperating with a second structure on at least one of said elongated implant elements in a form-fitting manner, such as to rotate said one elongated implant member relative to said central base structure.

Preferably, said dowel is cylindrical and comprises as first structure two ring-like enlargements at said one end, wherein said two ring-like enlargements are separated from each other by a distance. Correspondingly, the at least one of said elongated implant elements comprises as second structure two recesses preferably provided on a circular section. Both recesses are spaced apart by a length which corresponds to the distance separating the two ring-like enlargements. This provides a simple and easy to use drive for the intervertebral implant, as a linear movement of the dowel will exert a pulling or pushing force on said elongated implant member, resulting in a rotational movement of said elongated implant member.

Alternatively, the dowel may comprise a single protrusion which engages into a single groove provided on said one elongated implant member.

However, as a person having skill in the art will easily recognize the recess(es) as mentioned above may also be provided on said dowel while the ring-like enlargements or the protrusion may be located on said elongated implant member.

Further, any suitable type of form-fit interaction may be used for cooperation of said dowel with the elongated implant member.

A person having skill in the art will recognize that the elongated implant member cooperating with said worm or said dowel as explained above preferably is the at least one elongated implant member which has its gear teeth interlocked with the gear teeth of the at least two other elongated implant members.

Preferably, the dowel is arranged in a channel provided in said central base portion, said channel having an opening allowing the insertion of the instrument by a surgeon, such as to push or pull the dowel to move it relative to said central base portion.

Preferably, said dowel comprises a drive at a second end arranged opposite of said first end, such that an instrument to move said dowel may be inserted into said drive. More preferably, an outer thread is arranged on said second end, said outer thread cooperating with a matching inner thread provided in said central base portion of the intervertebral implant, preferably in said bore or channel. Hence, by imparting a turning motion to said dowel, the dowel will be linearly moved relative to said central base portion, thus imparting a pulling or pushing force onto said elongated implant member by means of the form-fit interaction of the two structures.

Preferably, each of the at least three elongated implant members comprises a lower surface and an upper surface, said two surfaces being arranged at an angle to each other.

Said angle more preferably is from 5° to 15°.

The two surfaces are located on the two sides of the elongated implant members intended to be in contact with the bone of adjacent vertebrae. By varying the angle of the upper and lower surfaces relative to each other allows to restore the natural lordotic or kyphotic curvature of the spine.

The present application further relates to a kit comprising multiple intervertebral implants according to the present invention, wherein the intervertebral implants are differently configured.

Preferably, the implants have incremental thicknesses between 8 and 20 mm. Hence, a surgeon may always select the intervertebral implant having an appropriate thickness for the intervertebral space to be treated.

Further preferably, the kit may also comprise multiple intervertebral implants according to the present invention having different combinations of elongated implant member lengths and/or elongated implant member widths.

As understood herein, the thickness of the intervertebral implant is understood as the maximal distance between the upper and lower surfaces of said elongated implant members and of said central base portion.

Preferably, the kit comprises intervertebral implants having varying angles between the lower surfaces and the upper surfaces of the elongated implant members and of the central base portion. This allows a surgeon to select an implant which has an optimal angle to restore the natural lordotic or kyphotic curvature of a patient's spine. Preferably, the angles vary from 1° to 15°.

In accordance with another aspect of the invention, a method is provided for replacing or repairing intervertebral disks which essentially includes the steps of: inserting the intervertebral implant in an undeployed state into an intervertebral space, attaching a deployment instrument to at least one of the elongated implant members, actuating the driving means so as to deploy the elongated implant members and removing the deployment instrument from the intervertebral implant.

In a special embodiment of the method the intervertebral implant is inserted into an intervertebral space by using a transforaminal technique.

Other advantageous embodiments and combinations of features result from the detailed description below and the totality of the claims.

A BRIEF DESCRIPTION OF THE DRAWINGS

Several embodiments of the invention will be described in the following by way of example and with reference to the accompanying drawings in which.

DETAILED DESCRIPTION OF THE INVENTION

Figure 1:
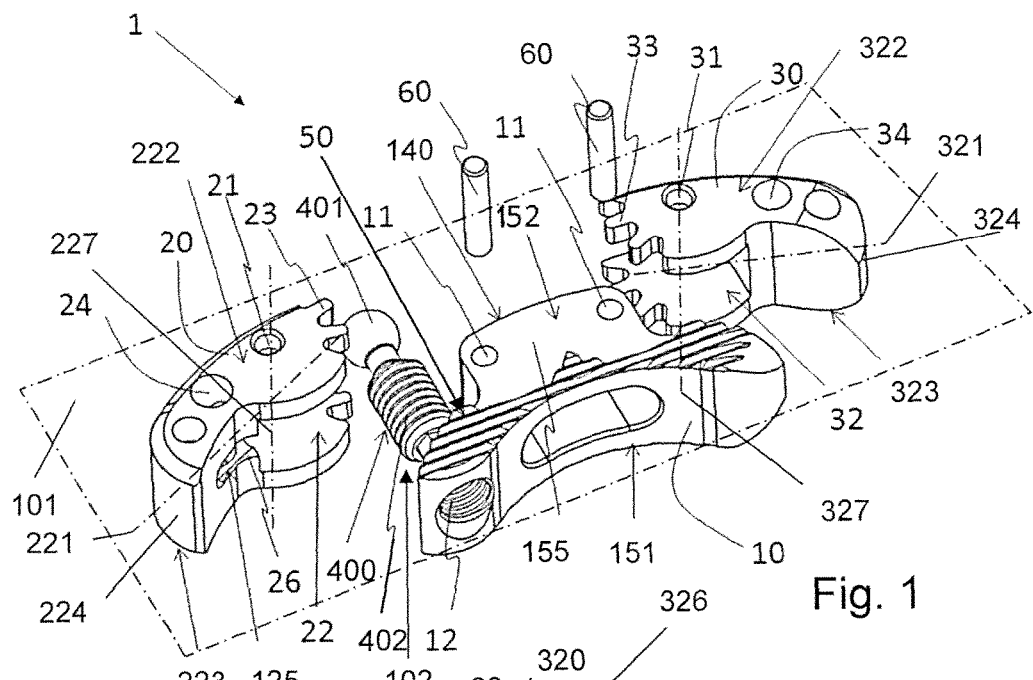
FIG. 1 illustrates an exploded view of a first embodiment of an intervertebral implant according to the invention.

FIGS. 1 to 5b illustrate a first embodiment the intervertebral implant 1 according to the invention which essentially comprises:
- a first elongated implant member 20 with a longitudinal axis 221, an upper surface 222 and a lower surface 223 for apposition to the endplates of two adjacent vertebrae, and with a lateral circumferential surface 224; and
- a second elongated implant member 30 with a longitudinal axis 321, an upper surface 322 and a lower surface 323 for apposition to the same endplates and with a lateral circumferential surface 324, wherein the first and second elongated implant members 20, 30 are rotatably coupled to a central body 10 for rotation in a central plane 101 essentially parallel to said upper and lower surfaces.

Furthermore, said first and second elongated implant members 20, 30 comprise each an inner end portion 225;325 which comprises a circular segment of a toothed wheel 220;320 with gear teeth 23;33 and with an axis of rotation 227;327 essentially orthogonal to the central plane 101 of the intervertebral implant and a free outer portion 226;326. The free outer portions 226;326 of said first and second elongated implant members 20, 30 are rotatable around the axis of rotation 227;327 of the circular segment of a toothed wheel 220;320 of their respective inner end portions 225; 325. Thereby, the circular segment of a toothed wheel 220 of said first elongated implant member 20 is in engagement with said circular segment of a toothed wheel 320 of the second elongated implant member 30. The circular segments of a toothed wheel 220;320 of said first and second elongated implant members 20;30 are located in a center portion 111 (FIG. 2) of said intervertebral implant 1 from which the elongated implant members (20, 30) are deployable.

In particular FIG. 1 shows the first embodiment of the intervertebral implant 1 in an exploded view. The intervertebral implant 1 comprises a first elongated implant member 20, a second elongated implant member 30, a central body 10 and two hinge-pins 60. Furthermore, the intervertebral implant 1 includes exemplarily but not limiting a driving means 102, which is configured as a dowel 400.

Each of the elongated implant members 20, 30 comprises an axis of rotation 227, 327 at a first end. Each axis of rotation 227, 327 is defined by a corresponding bore 21, 31 into which one of the two hinge-pins 60 is inserted. Furthermore, the elongated implant members 20, 30 each comprise a recess 22, 32 extending through the elongated implant member 20, 30 and intersecting with the bores 21, 31 wherein each recess 22, 32 is substantially perpendicularly arranged in reference to the respective axis of rotation 227, 327 defined by each bore 21, 31. Said first ends of the elongated implant members 20, 30 are of a half cylindrical shape and comprise a set of gear teeth 23, 33, circumferentially arranged around the axis of rotation defined by bores 21, 31. The gear teeth 23, 33 are arranged on both sides of the recesses 22, 32. Towards a second end, the elongated implant members 20, 30 each comprise an open cavity or pocket 24, 34 extending from a top surface 222, 322 to a bottom surface 223, 323, wherein the open cavities or pockets 24, 34 are shaped to receive bone graft material or a bone graft substitute, to promote bone ingrowth. Both elongated implant members 20, 30 are in the general shape of a segmental arc.

The central body 10 is a block shaped element in the general shape of a segmental arc which comprises, like the elongated implant members 20, 30, a top surface 150 and a bottom surface 151. At the apex 140 of the segmental arc, the central base portion comprises a part 155 with a top side 152 and a bottom side 153 which are spaced apart from the upper surface 150 and the lower surface 151, respectively, of the central body 10. The part 155 comprises two substantially parallel through-bores 11, extending form the top side 152 to the bottom side 153 of the part 155. Said through bores 11 are configured to each receive one of the two hinge-pins 60 such as to rotatably couple each of the elongated implant members 20, 30 to said central body 10.

The dowel 400 comprises a ball-head 401 and a threaded shaft 402. The ball-head 401 is engaged within a first channel 25 located on the inside of the first elongated implant member 20. The first channel 125 includes an opening 26 connecting said channel 125 to the outside and allowing the passage of the dowel 400 into said first channel 125. The threaded shaft 402 is engaged within a second channel 12 which comprises an internal thread cooperating with the threaded shaft 402.

Figure 2:
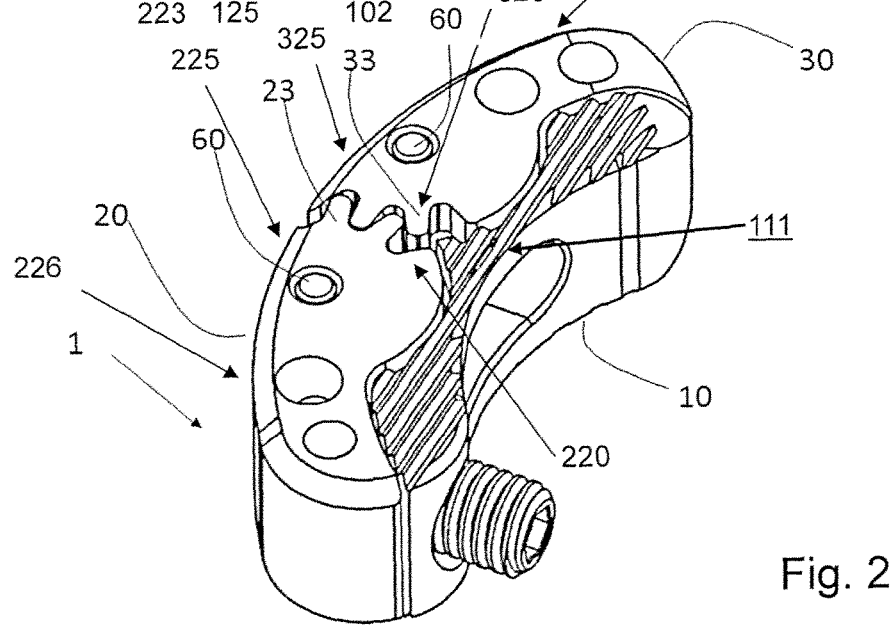
FIG. 2 illustrates the intervertebral implant according to FIG. 1 in an assembled configuration.

FIG. 2 shows the intervertebral implant 1 in an assembled state. The two elongated implant members 20, 30 are rotatably coupled to the central body 10 by means of the two hinge-pins 60 which are introduced into the bores 21, 31 of the elongated implant members 20, 30, and through the through bores 11 of the central body 10. The part 155 of the central body 10 is arranged within the recesses 22, 32 of the elongated implant members 20, 30. Both elongated implant members 20, 30 may only rotate around their rotation axis defined by the bores 21, 31. The sets of teeth 23, 33 are interlocked. As a result, upon actuation or rotation of the first elongated implant member 20, the second elongated implant member 30 will be actuated or rotated.

Note that the two elongated implant members 20, 30 are in the initial, unexpanded configuration. In this initial configuration, both elongated implant members 20, 30 abut onto the central body 10 along their entire length.

Figure 3A:
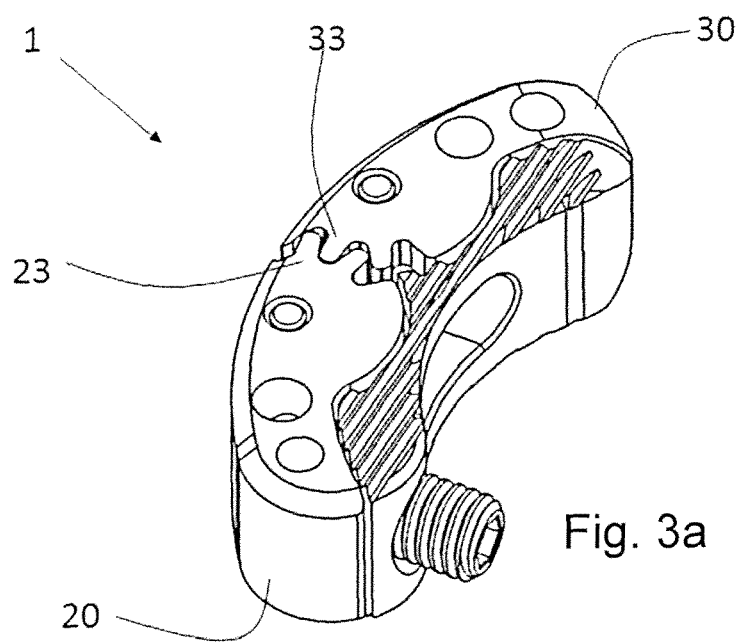
FIGS. 3a, 3b illustrate the expansion of the intervertebral implant according to FIG. 1.
Figure 3B:
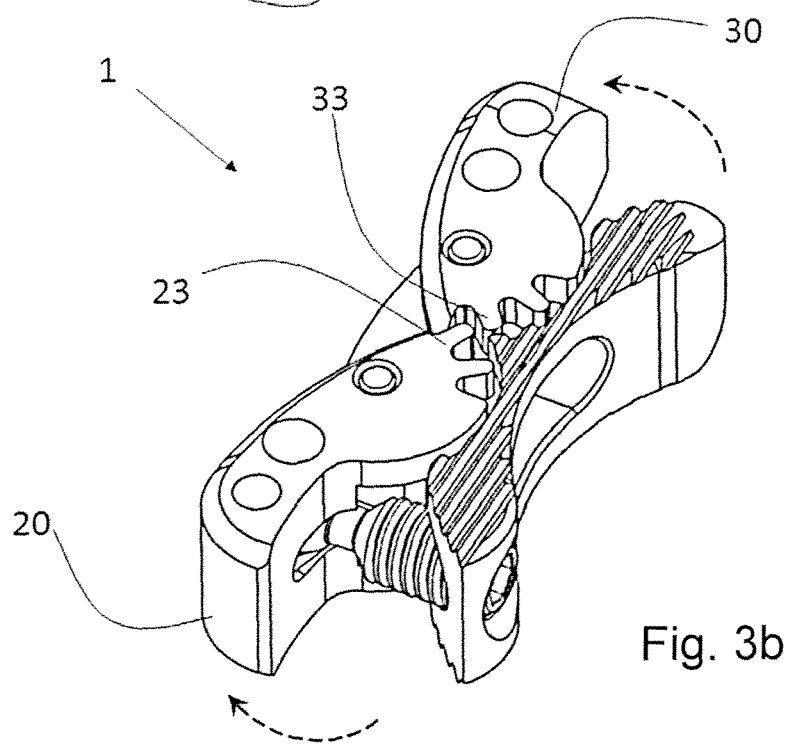

FIGS. 3a and 3b show the expansion of the intervertebral implant 1 according to FIG. 2. In a first initial and unexpanded configuration, the elongated implant members 20, 30 are abutting the central body 10 on their entire length. The intervertebral implant 1 has a substantially elongated, curved and narrow footprint in said first initial configuration, as shown in FIG. 3a. Upon actuation of the first elongated implant member 20, both elongated implant members 20, 30 rotate outwards, resulting in a second, expanded configuration as shown in FIG. 3b. This rotation is caused by the interaction of the gear teeth 23, 33 with each other. Hence, a rotation movement of one of said elongated implant members 20, 30 is transmitted by means of the gear teeth 23, 33 to the other elongated implant member 20, 30. In the second configuration the elongated implant members 20, 30 impart a generally X-shaped footprint to the intervertebral implant 1.

In an alternative embodiment the elongated implant members 20, 3 and the central body 10 may be substantially straight and form a substantially K-shaped footprint in the expanded configuration of the intervertebral implant 1.

In a variant, the elongated implant members 20, 30 may have a different length, for instance the first elongated implant member 20 may be longer than the second elongated implant member 30.

Figure 4A:
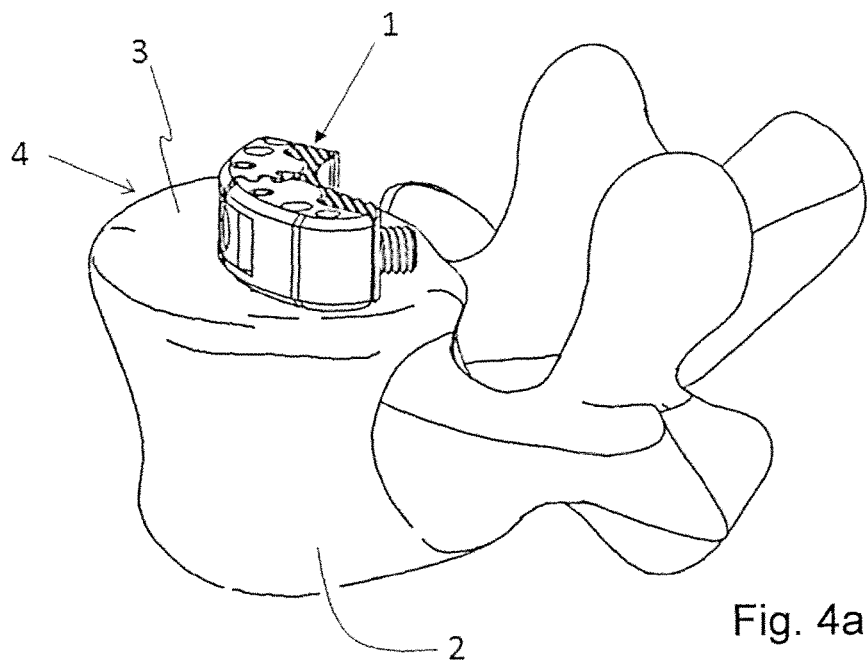
FIGS. 4a, 4b illustrate the intervertebral implant according to FIG. 1 arranged on a vertebral body.
Figure 4B:
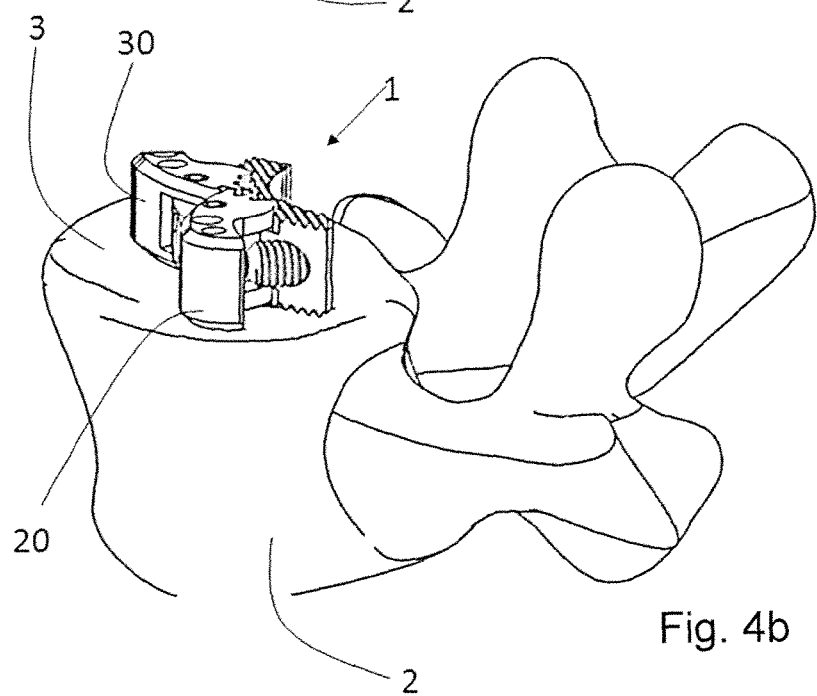
Figure 12A:
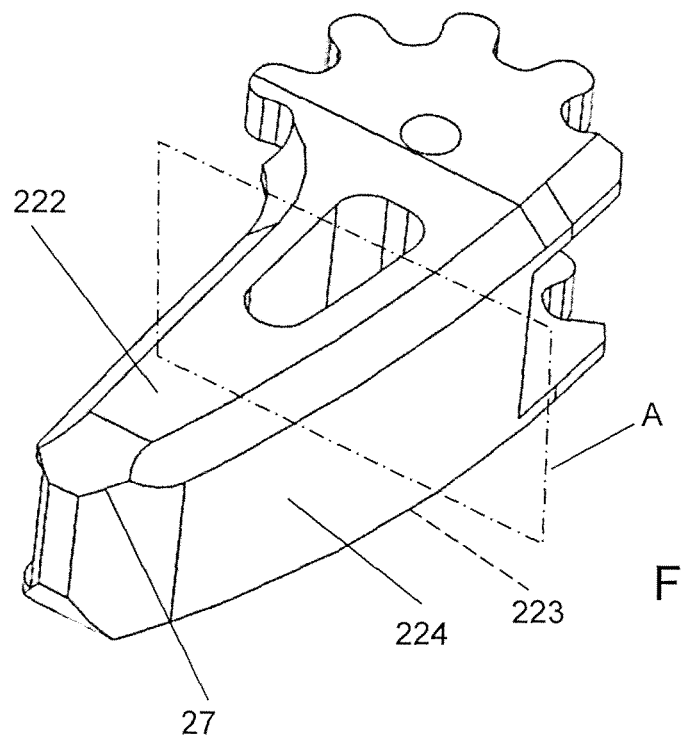
FIGS. 12a, 12b illustrate an elongated implant member according to a further embodiment of the intervertebral implant according to the invention.
Figure 12B:
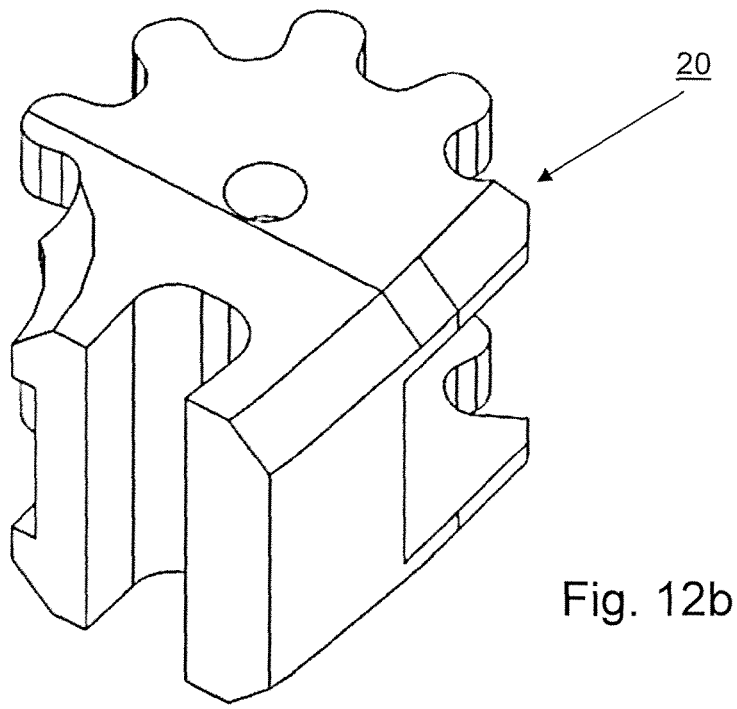

FIGS. 4a and 12b show the intervertebral implant 1 arranged on a vertebral body 2. The intervertebral implant 1 is thereby placed on the endplate 3 of the vertebral body 2 and occupies the intervertebral space 4 which would normally be occupied by the intervertebral disc. The adjacent vertebra on the other side of the intervertebral space 4 is not shown as it would cover the intervertebral implant 1 in the perspective of the figure. FIG. 4a shows the intervertebral implant 1 in the first, unexpanded configuration. In the second, expanded configuration, the elongated implant members 20, 30 are positioned close to the outer perimeter of the endplate 3 of the vertebral body 2, where the bone is denser, and withstands higher loads, as shown in FIG. 4b.

Figure 5A:
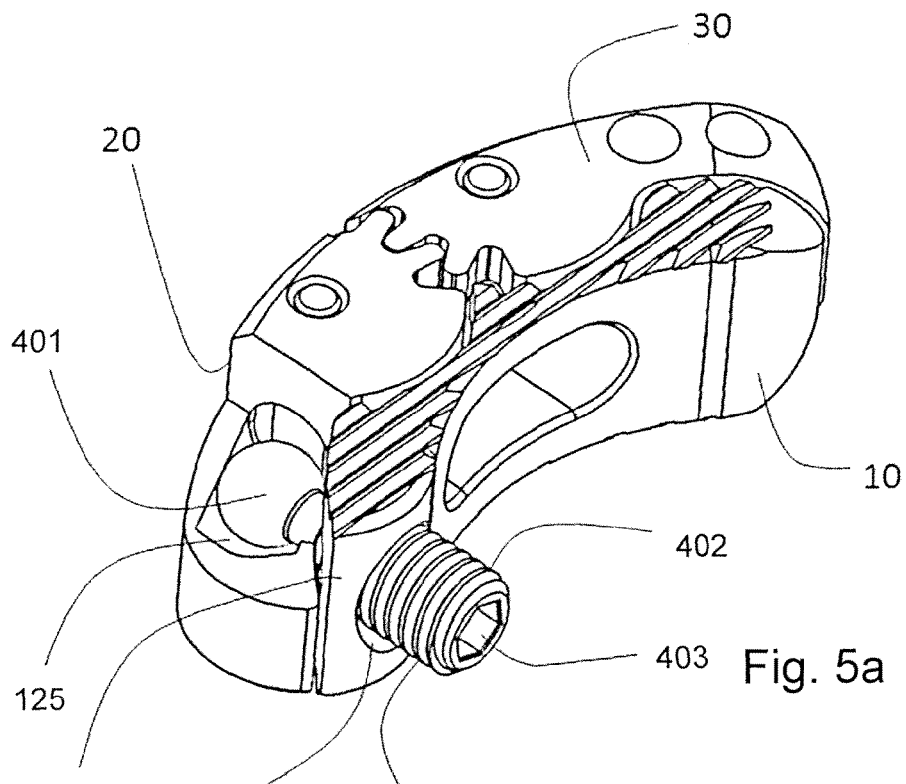
FIGS. 5a, 5b illustrate a second embodiment of an intervertebral implant according to the invention.
Figure 5B:
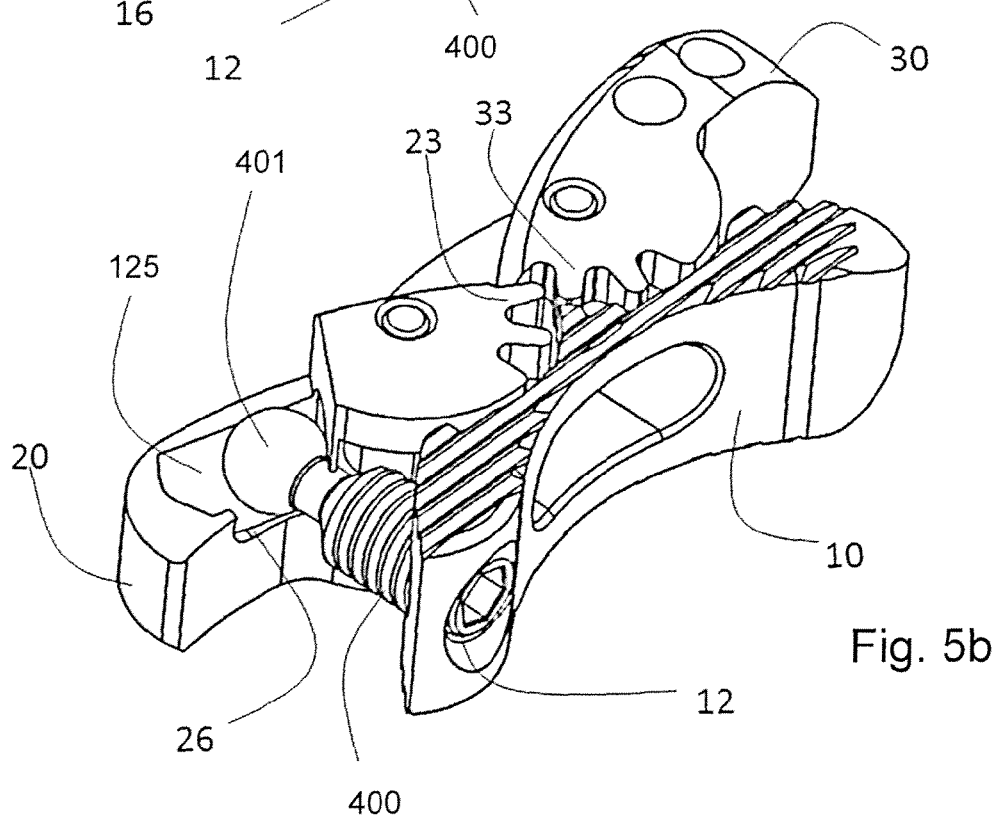

FIGS. 5a and 5b show the actuation mechanism of the intervertebral implant 1 in more detail. In both figures, the first elongated implant member 20 is shown in a cut-away view.

In the first, unexpanded configuration of the intervertebral implant 1, as shown in FIG. 5a, the ball head 401 of the dowel is located within the first channel 125 in a form-fitting manner. Linear movement of the dowel 400 within the second channel 12 will entail a rotational movement of the first elongated implant member 20 relative to the central body 10 by means of the interaction of the ball head 401 with the first channel 125. Further, the threaded shaft 402 comprises a drive 403. The threaded shaft 402 cooperates with the internal thread located in said first channel 125. By turning the dowel 400 via the drive 403, a linear translation of the dowel 400 will be caused by the cooperation of the threaded shaft 402 with the internal thread. Access to said drive 403 is made possible through the second channel 12, e.g. for a suitable instrument (not shown). In the embodiment shown, the drive 403 is configured as hexagonal drive, however, other drive types may also be used, such as e.g. a torx-drive. The central body 10 further includes an attachment portion 16 configured to be coupled to an insertion instrument (not shown). In the initial configuration, the dowel 400 is located at a retracted position within the second channel 12 and protrudes out of central body 10.

FIG. 5b shows the intervertebral implant 1 in the second, expanded configuration. In this configuration, the dowel 400 is located at an extended position within the second channel 12. By the translational movement of the dowel 400 from the retracted position as shown in FIG. 5a to said extended position, the ball head 401 pushed onto walls of the first channel 125 of the elongated member 20. This pushing force is translated in a rotational movement of the first elongated implant member 20, as its first end is coupled to the central body 10 by means of the first hinge-pin 60. Mediated by the engagement of the gear teeth 23, 33 the second elongated implant member 30 is likewise rotated.

Figure 6:
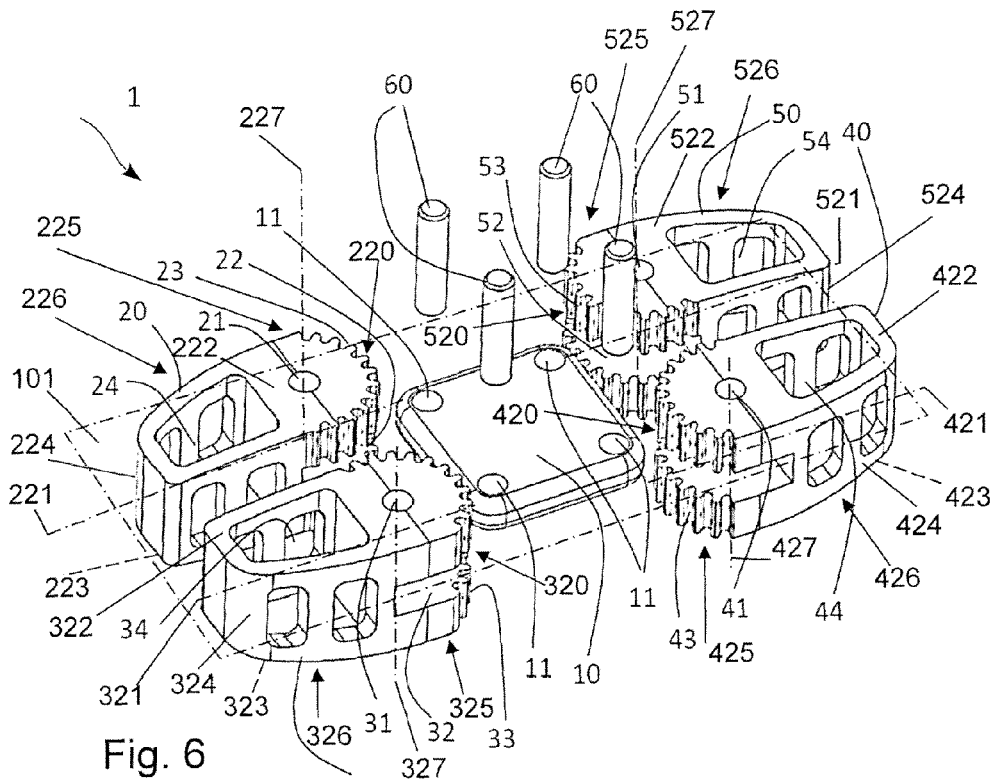
FIG. 6 illustrates an exploded view of a third embodiment of an intervertebral implant according to the invention.
Figure 7:
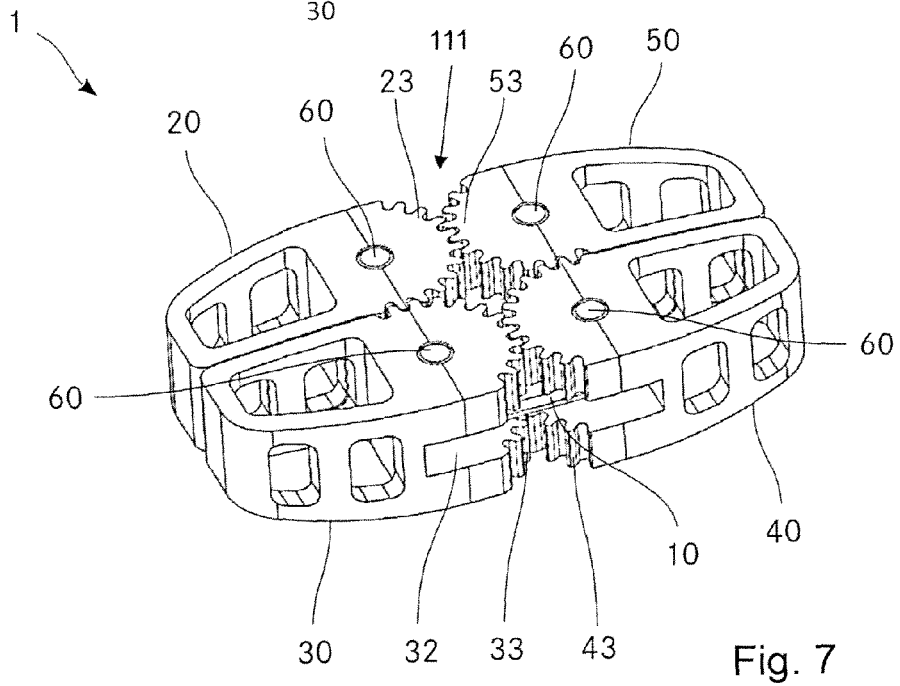
FIG. 7 illustrates the intervertebral implant according to FIG. 6 in an assembled configuration.

FIGS. 6 and 7 illustrate a third embodiment of the intervertebral implant 1 according to the invention, comprising three or more elongated implant members 20, 30, 40, 50, wherein said implant members 20, 30, 40, 50 are rotatably coupled to the central body 10. Furthermore, the circular segment of a toothed wheel 220;320;420;520 of each of said elongated implant members 20, 30, 40, 50 is in engagement with the circular segment of a toothed wheel 220;320;420;520 of two others of said elongated implant members 20, 30, 40, 50.

Each of the elongated implant members 20, 30, 40, 50 comprises a longitudinal axis 221;321;421;521, an upper surface 222;322;422;522, a lower surface 223;323;423;523 for apposition to the endplates of two adjacent vertebrae and a lateral circumferential surface 224;324;424;524. The elongated implant members 20, 30, 40, 50 are each rotatably coupled to the central body 10 for rotation in the central plane 101. Each of the elongated implant members 20, 30, 40, 50 comprises an inner end portion 225;325;425;525 which comprises a circular segment of a toothed wheel 220;320;420;520 with gear teeth 23;33;43;52 and with an axis of rotation 227;327;427;527 essentially orthogonal to the central plane 101 of the intervertebral implant 1 and a free outer portion 226;326;426;526. The free outer portions 226;326;427;527 of said four elongated implant members 20, 30, 40, 50 are rotatable around the axis of rotation 227;327;427;527 of the circular segment of a toothed wheel 220;320;420;520 of their respective inner end portions 225; 325;425;525. The circular segments of a toothed wheel 220;320;420;520 of the first, second, third and fourth elongated implant members 20;30;40;50 are located in the center portion 111 of said intervertebral implant 1 from which all of the elongated implant members 20, 30, 40, 50 are deployable.

FIG. 6 shows the third embodiment of the intervertebral implant 1 in an exploded view. The intervertebral implant 1 comprises four implant members 20, 30, 40, 50, a central body 10 and four hinge-pins 60.

Each of the elongated implant members 20, 30, 40, 50 comprises an axis of rotation 227;327;427;527 at an inner end portion 225;325;425;525. Each axis of rotation 227;327; 427;527 is defined by a corresponding bore 21, 31, 41, 51 into which one of the four hinge-pins 60 may be inserted. Furthermore, the elongated implant members 20, 30, 40, 50 each comprise a recess 22, 32, 42, 52 extending through the elongated implant member 20, 30, 40, 50 and intersecting with the bores 21, 31, 41, 51, wherein each recess 22, 32, 42, 52 is substantially perpendicularly arranged in reference to the respective axis of rotation 227;327;427;527 defined by each bore 21, 31, 41, 51. At said first end the elongated implant members 20, 30, 40, 50 are of a half cylindrical shape, and comprise a set of gear teeth 23, 33, 43, 53, circumferentially arranged around the axis of rotation defined by bores 21, 31, 41, 51. The gear teeth 23, 33, 43, 53 are arranged on both sides of the recesses 22, 32, 42, 52. Towards a second end, the elongated implant members 20, 30, 40, 50 each comprise an open cavity or pocket 24, 34, 44, 54 extending from the top surface to the bottom surface, wherein the open cavities or pockets 24, 34, 44, 54 are shaped to receive bone graft material or a bone graft substitute, to promote bone ingrowth.

The central body 10 is a block shaped element comprising four substantially parallel through-bores 11, extending form the top side and to the bottom side of the central base portion 10. Said through bores 10 are configured to each receive one of the four hinge-pins 60 such as to rotatably couple each of the elongated implant members 20, 30, 40, 50 to said central base portion.

FIG. 7 shows the intervertebral implant 1 in assembled configuration. All four elongated implant members 20, 30, 40, 50 are rotatably coupled to the central body 10 by means of four hinge-pins 60 which are introduced into the bores 21, 31, 41, 51 of the elongated implant members 20, 30, 40, 50 and through the through bores 11 of the central body 10. The central body 10 is arranged within the recesses 22, 32, 42, 52 of the elongated implant members 20, 30, 40, 50. All elongated implant members 20, 30, 40, 50 may only rotate around their hinge axis 21, 31, 41, 51. The sets of teeth 23, 33, 43, 53 all are interlocked, wherein each seat of gear teeth 23, 33, 43, 53 is interlocked into two adjacent sets of gear teeth 23, 33, 43, 53. For example, the first gear teeth 23 of the first elongated implant member 20 are engaged with the second gear teeth 33 of the second elongated implant member 30. These second gear teeth 33 are themselves further engaged with the third gear teeth 43 of the third elongated implant member 40. Said third gear teeth 43 are themselves engaged with the fourth gear teeth 53 of the fourth elongated implant member 50. Finally, said fourth gear teeth 43 are engaged 20 with the first gear teeth 23. As a result, upon actuation or rotation of any of the elongated implant members 20, 30, 40, 50, all the other implant members 20, 30, 40, 50 will be actuated or rotated.

Figure 8A:
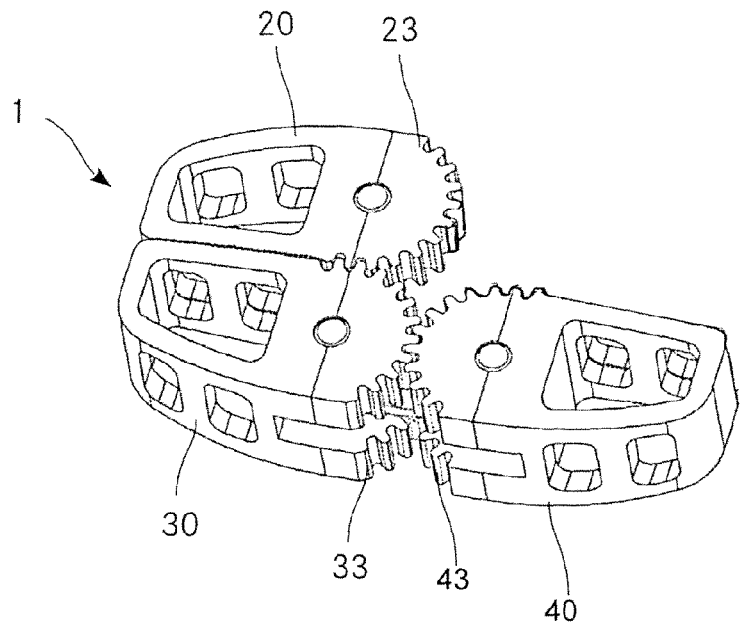
FIGS. 8a, 8b illustrate the expansion of a fourth embodiment of the intervertebral implant according to the invention.
Figure 8B:
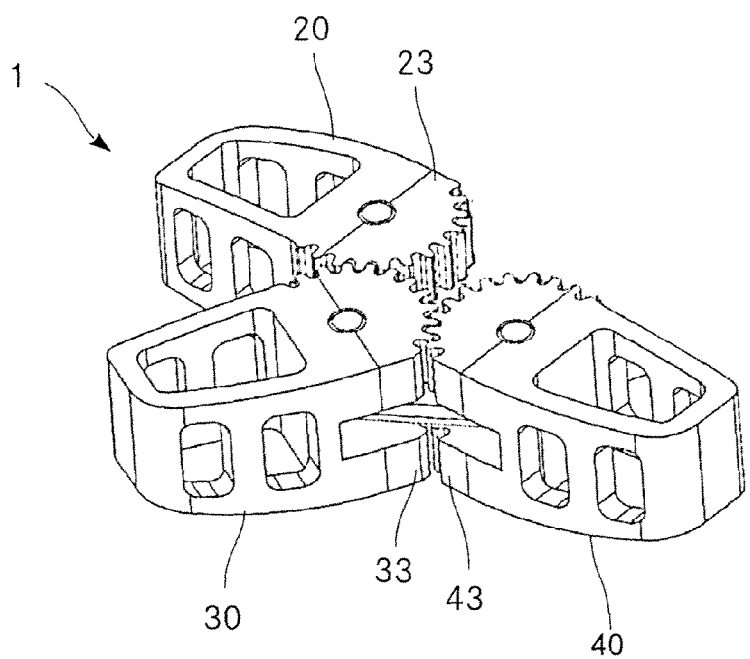

FIGS. 8a and 8b show a fourth embodiment of the intervertebral implant 1 according to the invention which differs from the third embodiment of FIG. 6 only therein that it comprises only three elongated implant members 20, 30, 40. In a first initial and unexpanded configuration, the elongated implant members 20, 30, 40 are pairwise oriented parallel to each other. The intervertebral implant 1 has a substantially L-shaped footprint in said first initial configuration, as shown in FIG. 8a. Upon actuation of one elongated implant member 20, 30, 40, all three implant members 20, 30, 40 rotate outwards, resulting in a second, expanded configuration as shown in FIG. 8b. This rotation is caused by the interaction of the gear teeth 23, 33, 43 with each other. Hence, a rotation movement of one of said elongated implant members 20, 30, 40 is transmitted by means of the gear teeth 23, 33, 43 to the other elongated implant members 20, 30, 40. In the second configuration the elongated implant members 20, 30, 40 impart an essentially Y-shaped footprint to the intervertebral implant 1.

Figure 9A:
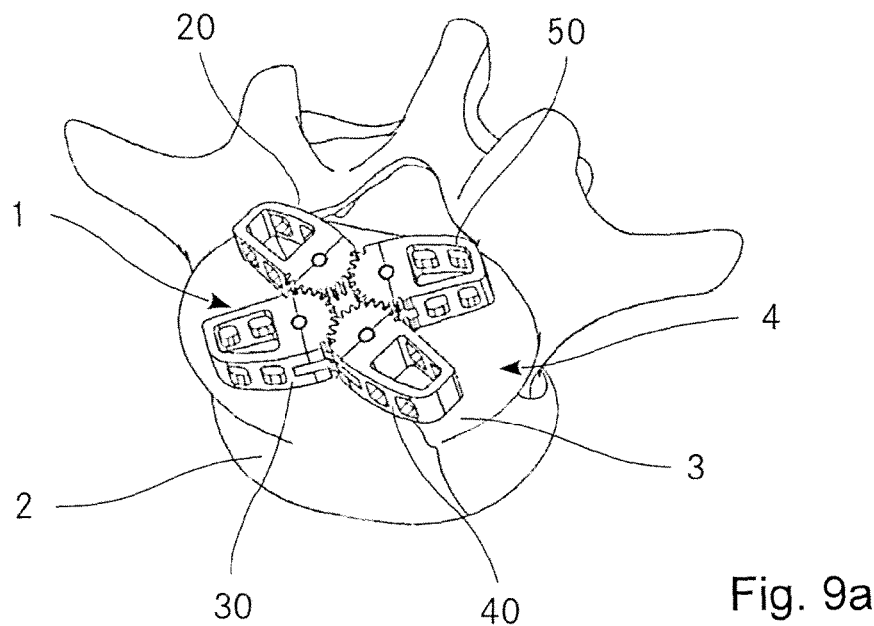
FIGS. 9a, 9b illustrate the intervertebral implant according to FIG. 1 arranged on a vertebral body.
Figure 9B:
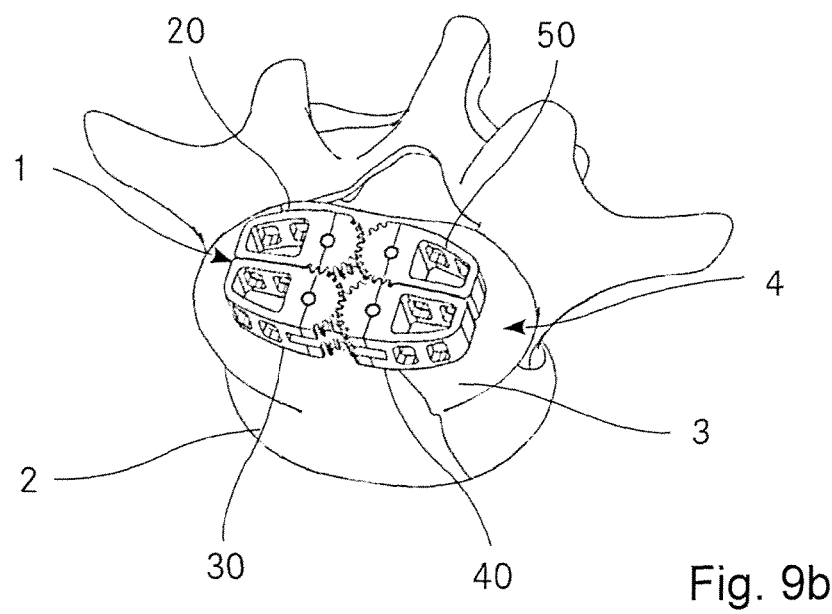

FIGS. 9a and 9b show the intervertebral implant 1 of FIGS. 6 and 7 arranged on a vertebral body 2. The intervertebral implant 1 is thereby placed on the endplate 3 of the vertebral body 2 and occupies the intervertebral space 4 which would normally be occupied by the intervertebral disc. The adjacent vertebra on the other side of the intervertebral space 4 is not shown as it would cover the intervertebral implant 1 in the perspective of the figure. FIG. 9a shows the intervertebral implant 1 in the first, unexpanded configuration. In the second, expanded configuration, the elongated implant members 20, 30, 40, 50 are positioned close to the outer perimeter of the endplate 3 of the vertebral body 2, where the bone is denser, and withstands higher loads, as shown in FIG. 9b.

The overall shape or footprint in said first and second configuration may have multiple shapes. For instance, the footprint may be quadratic, oblong, circular or irregularly shaped. Furthermore, the elongated implant members 20, 30, 40, 50 may have a different lengths, for instance the first elongated implant member 20 and the second elongated implant members 30 may be longer than the third elongated implant member 40 and the fourth implant member 50.

Figure 10A:
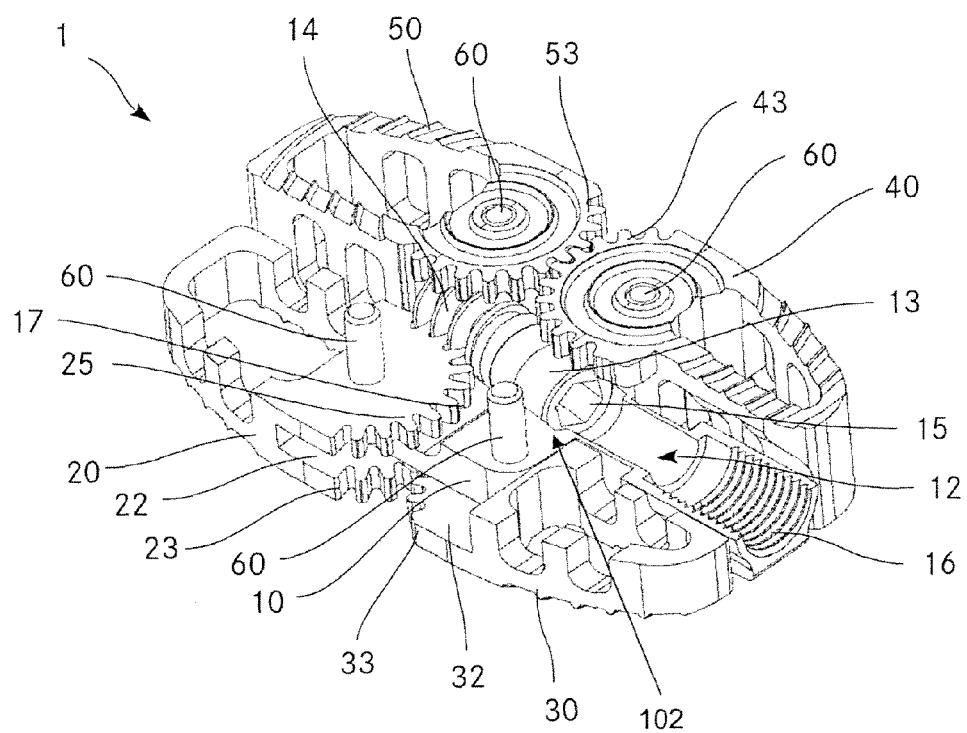
FIGS. 10a-10c illustrate a fifth embodiment of the intervertebral implant according to the invention comprising a worm.
Figure 10B:
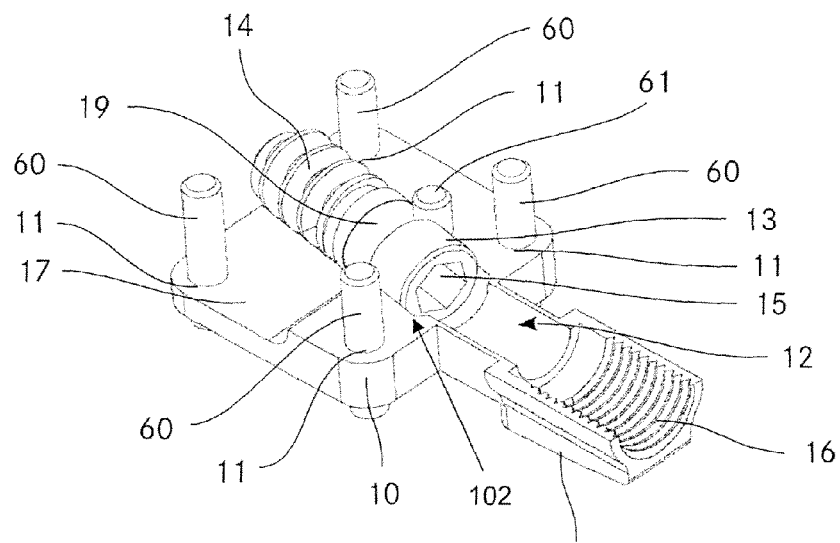
Figure 10C:
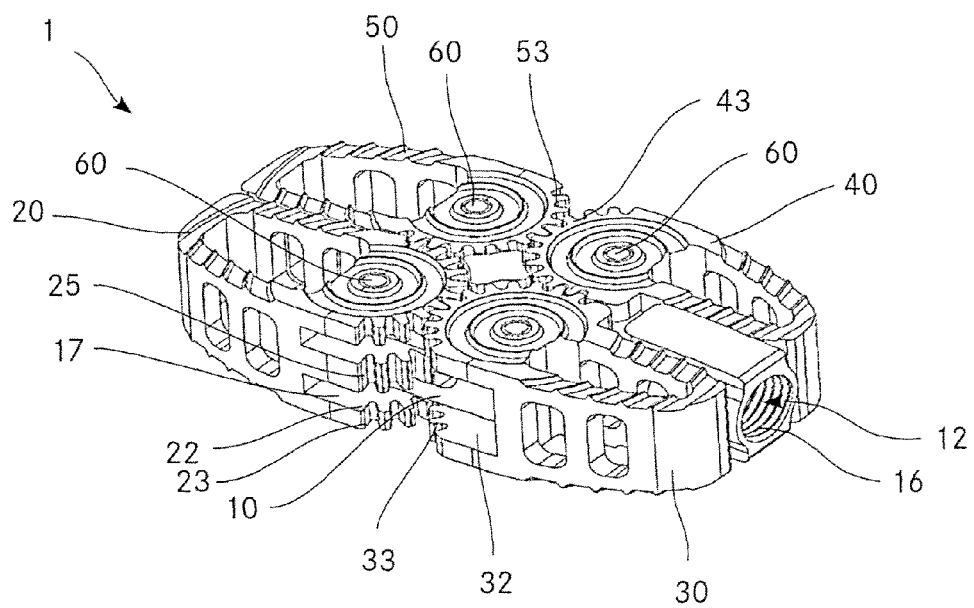

FIGS. 10a to 10c show a fifth embodiment of the intervertebral implant 1 according to the present invention. In FIG. 10a, the first elongated implant member 20 and the second elongated implant member 30 are shown in a cut-away view. In this embodiment, the central body 10 comprises a channel 12 into which a worm 13 acting as a driving means 102 is arranged. The worm 13 includes a worm thread 14 which is in engagement with secondary gear teeth 25 of the first elongated implant member 20. Rotation of the worm 13 within the channel 12 will rotate the secondary gear teeth 25, as the worm thread 14 and the secondary gear teeth 25 constitute a worm-gear, and thus the first elongated implant member 20 will be rotated around the respective gear-pin 60. Such as to impart a rotation onto worm 13, a drive 15 is arranged on one end of said worm 13. Access to said drive 15 is made possible through the channel 12, e.g. for a suitable instrument. In the embodiment shown, the drive 15 is configured as hexagonal drive, however, other drive types may also be used, such as e.g. a torx-drive. The channel 12 includes an attachment portion 16 configured to be coupled to an insertion instrument. In the embodiment shown, the attachment portion 16 comprises a thread configured to cooperate with a matching thread of an insertion instrument (not shown). The secondary gear teeth 25 are arranged between the central base portion 10 and the first gear teeth 23. Such as to provide enough space for said secondary gear teeth 25, the central body 10 includes a groove 17.

FIG. 10b is a detailed view of the central body 10. The four hinge-pins 60 are shown inserted into their respective through-bores 11. As may be seen, the channel 12 extends further than the core of the central body 10 into a protrusion 18 which is sized and shaped such as to lie between the second elongated implant element 20 and the third elongated implant element 30 as shown in FIG. 10a. The worm 13 includes the worm thread 14 as well as a notch 19. The notch 19 cooperates with a peg 61 which protrudes from the central base portion 10. The cooperation of the notch 19 with the peg 61 keeps the worm 13 at the same position within the channel 12 while still allowing rotational movement of the worm 13. Further, the groove 17 is recognizable around the area of the hinge-pin 60 which will be coupled to the first elongated implant member 20.

FIG. 10c shows the fifth embodiment of the intervertebral implant 1 according to FIG. 10a in an overall view. All four elongated implant members 20, 30, 40, 50 are arranged generally parallel to each other, i.e. the intervertebral implant 1 is in the un-expanded configuration. As may be seen on this picture, the first elongated implant member 20 comprises a set of secondary gear teeth 25 which cooperate with the worm thread (not shown in this picture).

Figure 11A:
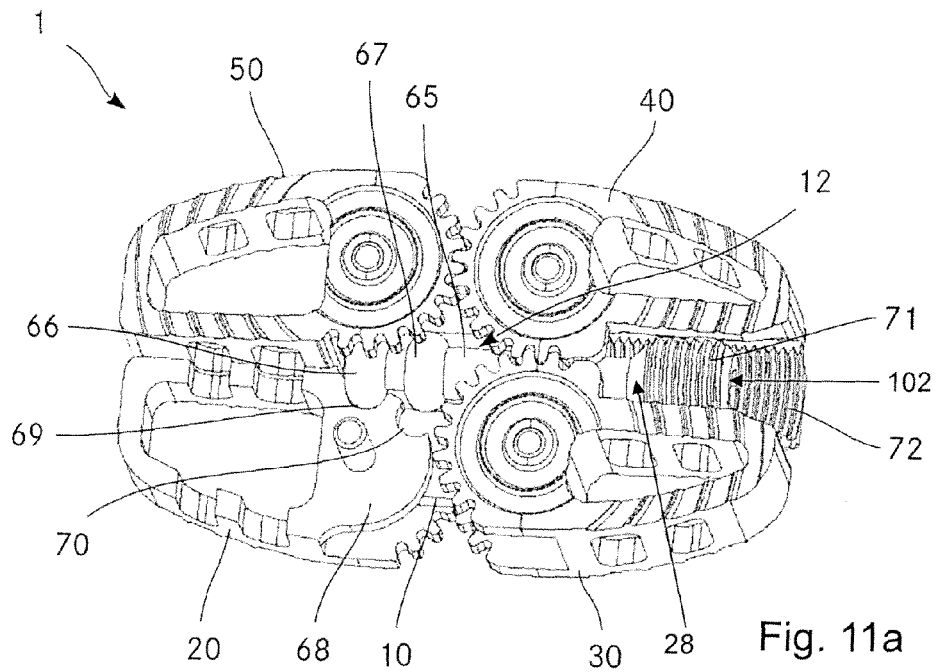
FIGS. 11a, 11b illustrate a sixth embodiment of the intervertebral implant according to the invention comprising a dowel.
Figure 11B:
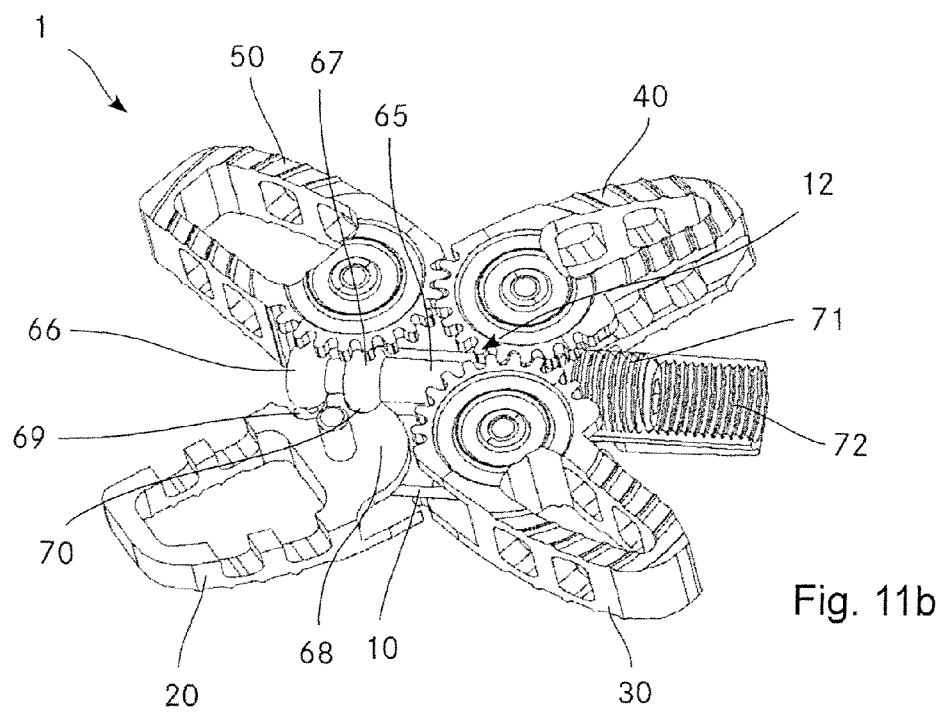

FIGS. 11a and 11b show a sixth embodiment of the intervertebral implant 1 according to the present invention. In FIG. 11a, the first elongated implant member 20 is shown in a cutaway view. Compared to the embodiment as shown in FIGS. 10a and 10b, the present embodiment comprises a dowel 65 instead of a worm 13 arranged in the channel 12 of the central body 10. The dowel 65 may be linearly translated within the channel 12 and comprises a first structure including a first ring-like enlargement 66 and a second ring-like enlargement 67. Said first structure cooperates with a second structure arranged on a circular section 68 of the first elongated implant member 20. The second structure includes a first recess 69 and a second recess 70. In the first, un-expanded configuration of the intervertebral implant 1 as shown in FIG. 11a, the first ring-like enlargement 66 is located within the first recess 69 in a form-fitting manner. Linear movement of the dowel 65 within the channel 12 will hence entail a rotational movement of the first elongated implant member 20 by means of the interaction of the first ring-like enlargement 66 with the first recess 69. Further, the peg 65 comprises a threaded head 71 with a drive. The threaded head 71 cooperates with an internal thread 72 located in said channel 12. By turning the dowel 65 via the drive, a linear translation of the dowel 65 will be mediated by the cooperation of the threaded head 71 with the internal thread 72.

FIG. 11b shows the sixth embodiment of the intervertebral implant 1 in the second, expanded configuration. In this configuration, the dowel 65 is at a position within the channel 12 which is more towards said first elongated implant member 20 and said fourth elongated implant member 50 than in the first, un-expanded configuration shown in FIG. 11a. By the translational movement of the dowel 65, the first ring-like enlargement 66 pushed onto the first recess 69. This pushing force was translated in a rotational movement of the first elongated implant member 20. Mediated by the engagement of the gear teeth 23, 33, 43, 53 all of the elongated implant members 20, 30, 40, 50 are rotated. As the first ring-like enlargement 66 disengages from the first recess 69 after a certain distance of the translation of the dowel 65, and hence no further rotational movement of the four elongated implant members 20, 30, 40, 50 would be possible, the second recess 70 has been foreseen. Said second recess 70 is brought into form-fitting engagement with the second ring-like enlargement 67 of the dowel 65 after a predefined rotation of the first elongated implant member 20. This form-fitting engagement allows to impart further rotational movement to the first elongated implant member 20 by further linear movement of the dowel 65.

Figure 13A:
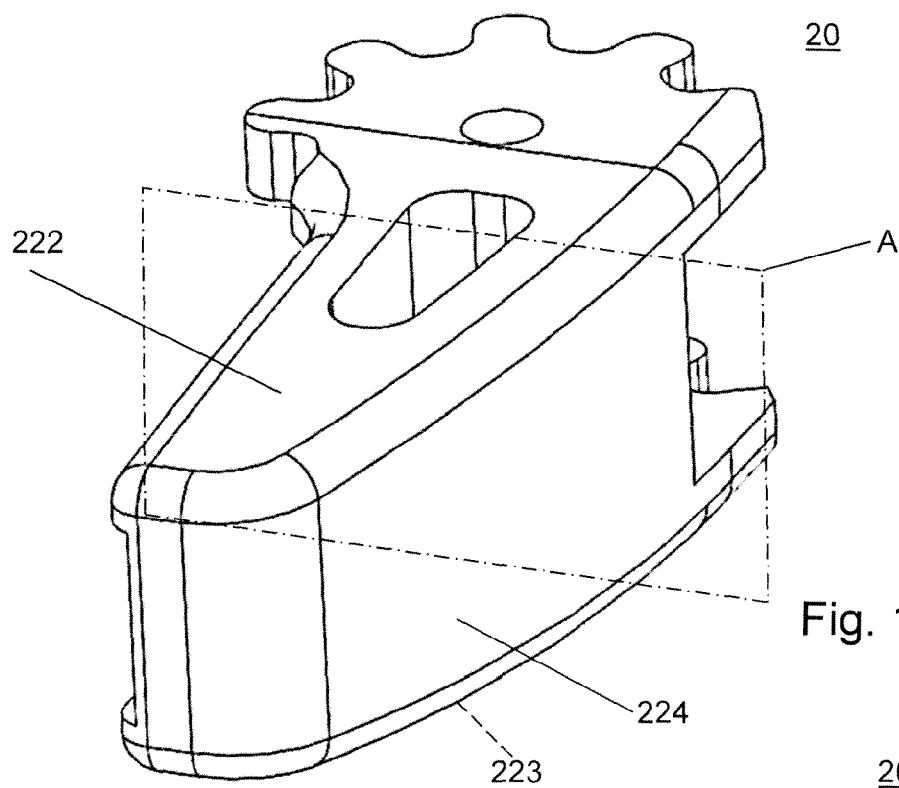
FIGS. 13a, 13b illustrate an elongated implant member according to again a further embodiment of the intervertebral implant according to the invention.
Figure 13B:
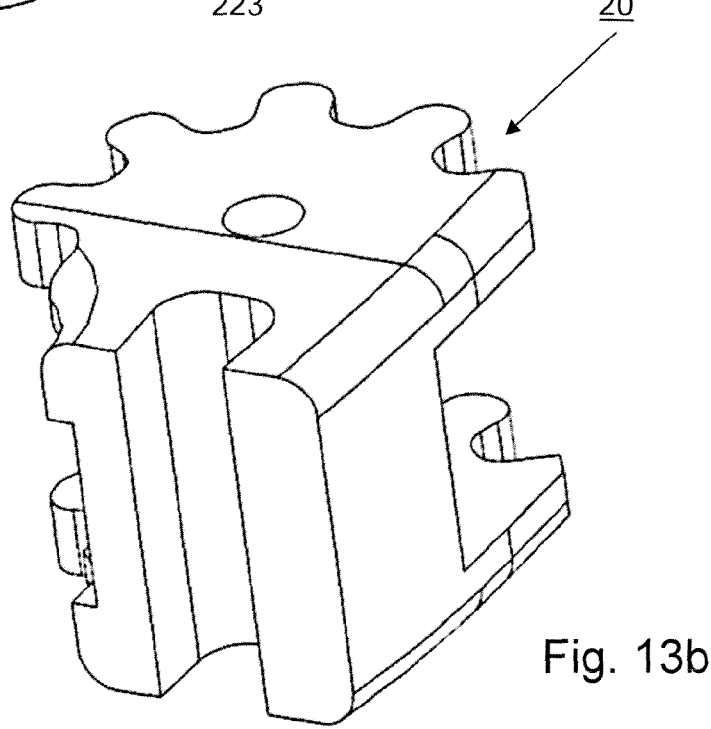

FIGS. 12a and 12b exemplarily illustrate a first elongated implant member 20 wherein the edges 27 between the lateral circumferential surface 224 and the upper surface 222, respectively the lower surface 223 of said elongated implant member 20 are chamfered. FIG. 12b is a cross-section in plane A in FIG. 11a. It will be apparent for those skilled in the art the this configuration is applicable to each of the elongated implant members 20, 30, 40, 50 in any of the above described embodiments of the intervertebral implant 1 according to the invention. In FIGS. 13a and 13b the first elongated implant member 20 is again exemplarily illustrated with the only difference to FIGS. 12a and 12b that the edges 27 between the lateral circumferential surface 224 and the upper surface 222, respectively the lower surface 223 of said elongated implant member 20 are rounded instead of chamfered.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. An intervertebral implant comprising:
   a first elongated implant member having a longitudinal axis, an upper surface and a lower surface for apposition to endplates of two adjacent vertebrae, and a lateral circumferential surface;
   a second elongated implant member having a longitudinal axis, an upper surface and a lower surface for apposition to said endplates of two adjacent vertebrae, and a lateral circumferential surface; and
   a central body, said first and second elongated implant members each being separately rotatably coupled to the central body for rotation in a central plane parallel to said upper and lower surfaces;
   wherein said first and second elongated implant members each comprise
   an inner end portion, which comprises a segment of a toothed wheel with gear teeth and an axis of rotation orthogonal to the central plane of the intervertebral implant, and
   a free outer portion,
   wherein said free outer portions of said first and second elongated implant members are rotatable around the axis of rotation of the segment of the toothed wheel of their respective inner end portions,
   wherein the segment of a toothed wheel of said first elongated implant member is in engagement with said segment of a toothed wheel of the second elongated implant member,
   wherein the segments of a toothed wheel of said first and second elongated implant members are located in a center portion of said intervertebral implant from which the elongated implant members are deployable, and
   wherein said elongated implant members and the central body form an X-shaped footprint in an expanded configuration of the intervertebral implant.

2. The intervertebral implant according to claim 1, wherein said central body is in a form of a segmental arc and said elongated implant members are coupled to said central body at an apex of said segmental arc.

3. The intervertebral implant according to claim 1, wherein the elongated implant members are in the shape of a segmental arc and abut with said central body along their entire length in an unexpanded configuration of the intervertebral implant.

4. The intervertebral implant according to claim 1, further comprising:
   a) a third elongated implant member having a longitudinal axis, an upper surface and a lower surface for apposition to said endplates of two adjacent vertebrae and a lateral circumferential surface, and being rotatably coupled to the central body, wherein:
   b) the third elongated implant member comprises:
      i) an inner end portion which comprises a segment of a toothed wheel with gear teeth and with an axis of rotation orthogonal to the central plane of the intervertebral implant; and
      ii) a free outer portion; and wherein
      iii) the free outer portion of the third second elongated implant member is rotatable around the axis of rotation of the segment of a toothed wheel of its respective inner end portion;
   c) whereby the segment of a toothed wheel of said third elongated implant member is in engagement with a segment of a toothed wheel of one of the first and second elongated implant members, and wherein d) the segment of a toothed wheel of said third elongated implant member is located in a center portion of said intervertebral implant from which the elongated implant members are deployable.

5. The intervertebral implant according to claim 1, comprising at least three elongated implant members, said at least three elongated implant members being rotatably coupled to the central body, and wherein a segment of a toothed wheel of at least one of said at least three elongated implant members is in engagement with a segment of a toothed wheel of two other of said at least three elongated implant members.

6. The intervertebral implant according to claim 1, wherein the central body is provided with driving means for rotating said first and second elongated implant members around their respective axis of rotation from a collapsed configuration, suitable for insertion into an intervertebral space between two adjacent vertebrae, to an expanded configuration when positioned between the endplates of two adjacent vertebrae.

7. The intervertebral implant according to claim 1, wherein expansion of the intervertebral implant is reversible.

8. The intervertebral implant according to claim 1, wherein expansion of the intervertebral implant is of a stepless nature.

9. The intervertebral implant according to claim 1, wherein said elongated implant members are of unequal length.

10. The intervertebral implant according to claim 1, wherein said elongated implant members comprise at least one open cavity or pocket for receiving bone graft material.

11. The intervertebral implant according to claim 1, wherein said elongated implant members are configured as cages for receiving bone graft material.

12. The intervertebral implant according to claim 1, wherein the upper surfaces and the lower surfaces of said elongated implant members are arranged at an angle different from 0° to each other.

13. The intervertebral implant according claim 1, wherein the lower surfaces and the upper surfaces of said elongated implant members are parallel to each other.

14. The intervertebral implant according to claim 1, wherein the elongated implant members are parallel in an unexpanded configuration of the intervertebral implant.

15. A kit comprising multiple intervertebral implants according to claim 1, wherein the implants are differently configured.

16. A method for replacing or repairing intervertebral disks comprising:

A) inserting an intervertebral implant according to claim 10 in an undeployed state into an intervertebral space;

B) attaching a deployment instrument to at least one of the elongated implant members;

C) actuating the driving means so as to deploy the elongated implant members; and D) removing the deployment instrument from the intervertebral implant.

17. The method according to claim 16, wherein the intervertebral implant is inserted into an intervertebral space by using a transforaminal technique.

* * * * *